United States Patent [19]

Kitson

[11] Patent Number: 4,611,085

[45] Date of Patent: Sep. 9, 1986

[54] VAPOUR PHASE HYDROGENATION OF ESTERS

[75] Inventor: Melanie Kitson, Staines, England

[73] Assignee: The British Petroleum Company p.l.c., London, England

[21] Appl. No.: 678,567

[22] PCT Filed: Apr. 18, 1984

[86] PCT No.: PCT/GB84/00133

§ 371 Date: Nov. 30, 1984

§ 102(e) Date: Nov. 30, 1984

[87] PCT Pub. No.: WO84/04297

PCT Pub. Date: Nov. 8, 1984

[51] Int. Cl.$^4$ ............................................. C07C 29/136
[52] U.S. Cl. .................................... 568/885; 562/607; 568/864
[58] Field of Search ................................ 568/885, 864

[56] References Cited

U.S. PATENT DOCUMENTS

| | | | |
|---|---|---|---|
| 2,322,095 | 6/1943 | Schmidt | 568/885 |
| 2,607,807 | 8/1952 | Ford | 568/885 |
| 3,829,448 | 8/1974 | Kanetaka et al. | 568/885 |
| 4,010,197 | 3/1977 | Toriya et al. | 568/864 |
| 4,214,106 | 7/1980 | Freudenberger et al. | 568/864 |
| 4,346,240 | 8/1982 | Grey et al. | 568/885 |
| 4,398,039 | 8/1983 | Pesa et al. | 568/885 |
| 4,456,775 | 6/1984 | Travers et al. | 568/885 |

*Primary Examiner*—J. E. Evans
*Attorney, Agent, or Firm*—Morgan, Finnegan, Pine, Foley & Lee

[57] ABSTRACT

The present invention relates to the vapour phase hydrogenation of carboxylic acid esters to give alcohols. More particularly, this invention pertains to a process for the production of an alcohol by hydrogenation of an ester with a hydrogenation catalyst comprising a Group VIII element, a promoter, and a carbon support. This process is characterized in that (1) the Group VIII element is ruthenium, nickel, or rhodium, (2) the promoter is introduced on to the carbon as a water stable compound of Group IA, IIA metal, a lanthanide or actinide, and (3) the carbon has a BET surface area of at least 100 m$^2$/g, and a ratio of BET to basal plane surface area not greater than 4:1, and (4) the hydrogenation is carried out in the vapor phase at a temperature in the range 100° C. to 400° C. at a total space velocity of 100 to 120,000.

9 Claims, No Drawings

VAPOUR PHASE HYDROGENATION OF ESTERS

The present invention relates to the vapour phase hydrogenation of carboxylic acid esters to give alcohols.

It is disclosed in GB Pat. No. 1 471 233 that catalysts prepared from transition metal compounds and a defined carbon support may be used for certain hydrogenation reactions. However there is no suggestion that such catalysts would be useful for the hydrogenation of carboxylic esters to give alcohols. This is a very difficult reaction to carry out with adequate selectivity. Attempts to hydrogenate carboxylic acid esters often give the acid and a hydrocarbon rather than the alcohol. There is nothing in GB Pat. No. 1 471 233 to suggest that the catalysts described therein would be in any way suitable for the hydrogenation of esters to give alcohols.

U.S. Pat. No. 4,346,240 discloses a process for the liquid phase hydrogenation of esters to give alcohols. The catalyst used is prepared from transition metals, activated carbon, and alkali metals. The alkali metal is introduced onto the carbon either as the free metal or as a cationic form with a very strongly basic anion. When an alkali metal compound is used, it is introduced onto the support using solvents which lack free hydroxyl groups. Water could not be used as a solvent for the alkali metal compounds disclosed in U.S. Pat. No. 4,346,240.

U.S. Pat. No. 4,346,240 states that the hydrogenation may be carried out at temperatures in the range 0°–150° C., but a preference is expressed for temperatures of 25°–100° C. It is stated that higher temperatures may be used and are considered to be equivalent to the temperature ranges given.

In a liquid phase process any increase in the reaction temperature will cause an increase in the reaction pressure necessary to keep the reaction in the liquid phase, which will increase the cost of the process. In these specific examples of U.S. Pat. No. 4,346,240 reaction pressures of 770 kPa (90 psig) and 1150 kPa (150 psig) are used. Very long contact times are also used. The shortest time was two hours but in most examples the reaction time was 24 hours.

It would be desirable to be able to prepare alcohols from esters by a continuous vapour phase process rather than by the liquid phase batch process disclosed in U.S. Pat. No. 4,346,240. However in order to obtain a useful production rate it is necessary to use comparatively short contact times. In order to obtain a useful rate of reaction with a short contact time, it is necessary to use a relatively high reaction temperature.

U.S. Pat. No. 4,346,240 discusses several known catalysts used for the hydrogenation of esters. These use temperatures above 150° C., but also use very high pressures (13.8 MPa to 20.7 MPa) so that the process will be a liquid phase process. The catalysts mentioned are Raney nickel, copper chromite or zinc-chromium oxide. However if such catalysts are used in vapour phase processes instead of liquid phase processes the elevated temperature the results deteriorate markedly. Thus until now it has not been possible to carry out the vapour phase hydrogenation of esters to alcohols in a satisfactory manner.

There is nothing in U.S. Pat. No. 4,346,240 to suggest that the nature of the carbon support is in any way important for the hydrogenation of esters or that ester hydrogenation catalysts can be made without the use of promoters in the form of free metals or in the form of special ionic forms unstable to water.

According to the present invention the process for the production of an alcohol by hydrogenation of an ester with a hydrogenation catalyst comprising a Group VIII element, a promoter, and a carbon support is characterized in that (1) the Group VIII element is ruthenium, nickel or rhodium, (2) the promoter is introduced onto the carbon as a water stable compound of a Group IA, IIA metal a lanthanide or actinide, and (3) the carbon has a BET surface area of at least 100 m$^2$/g, and a ratio of BET to basal plane surface area not greater than 4:1, and (4) the hydrogenation is carried out in the vapour phase at a temperature in the range 100° C. to 400° C. at a total space velocity of 100 to 120,000.

Reference is made in this specification to elements from various groups of the Periodic Table. The Periodic Table referred to is that published by the United Kingdom Patent Office in the Classification Manual for Section C2 of the Patent Office classification dated 1980. In this Table Group IA includes the elements from hydrogen to francium, and Group IIA includes the elements beryllium to radium.

In this specification the term "alkali metal" means the Group IA elements excluding hydrogen and lithium and the term "alkaline earth metal" means the Group IIA elements excluding beryllium and magnesium.

The process of the present invention may be applied to any ester which can be vapourised under the temperature conditions specified. The ester may be an ester of a carboxylic acid having from 1 to 20 carbon atoms. The ester is preferably an ester of an alcohol having from 1 to 5 carbon atoms. The total number of carbon atoms in the molecule is preferably not more than 20. The alcohol is preferably a primary alcohol. The process of the present application is particularly applicable to the production of ethanol from ethyl acetate.

We have found that it is necessary to select certain Group VIII elements in order to obtain satisfactory selectivities to ethanol. Thus the Group VIII metal used is ruthenium, nickel or rhodium. However the use of ruthenium or nickel is preferred. The Group VIII metal is present in the active catalyst as the metal and, although it may be reduced from a higher oxidation state by the hydrogen fed in with the ester it is preferred to carry out a previous reduction step before the catalyst is brought into contact with the ester.

The Group VIII metal may be introduced onto the carbon support in the form of a solution of a compound of the metal in a suitable solvent. The solvent may be a non-aqueous solvent where a suitable soluble Group VIII compound soluble in the solvent is available e.g. solutions of acetylacetonates in organic solvents. However it is preferred to use water-soluble Group VIII metal compounds in the form of their aqueous solutions for examples aqueous solutions of halides and nitrates.

The nature of the Group VIII metal compound is not important. However it is known that certain components are preferably excluded from promoted transition metal/carbon catalysts. Thus the presence of chloride ion in the final catalyst is believed to be undesirable and methods of preparing the catalyst are preferably used which do not result in the presence of chloride, or other halide, ions in the finished catalyst. The person skilled in the art of making hydrogenation catalysts will be familiar with components which it is desirable to exclude from promoted transition metal/carbon catalysts.

The Group VIII elements are conveniently introduced onto the support as solutions of the chlorides. The presence of alkali metal will bind the chloride to the catalyst so that it is not removed when the catalyst is treated with hydrogen. Therefore, when using halides of a Group VIII element, it is desirable to introduce the halides onto the support before Group IA or Group IIA elements are present, and to remove the halide e.g. by treating the impregnated carbon with hydrogen before the Group IA or Group IIA element is introduced.

Any water or other solvent present in the support after the Group VIII element has been deposited is preferably removed before proceeding to the next stage of catalyst preparation, e.g. hydrogenation. This may be done by heating the catalyst support at temperatures in the range 100° to 150° C.

The Groups IA or IIA metal compound is a water-stable compound i.e. it can be brought into contact with water without decomposition unlike the organometallic compounds disclosed in U.S. Pat. No. 4,346,240. The most convenient way of depositing the water-stable compound on the carbon support is by impregnation with an aqueous solution, and it is therefore preferred to use water soluble compounds. The solubility in water is preferably sufficient to give the required content of Group IA or IIA metal in a single impregnation step. Thus the solubility may for example be at least 1 g/100 g at 20° C. The Group IA or IIA metal is preferably an alkaline or alkaline earth metal. Examples of water-soluble salts which can be used to prepare the catalyst are nitrates, carbonates, and acetates.

The concentration of the aqueous solution is preferably sufficient to deposit the desired quantity of Group VIII compound in a single impregnation step.

After the required quantity of Group IA or Group IIA has been deposited, the impregnated carbon is preferably dried for example at temperatures of 100° to 150° C.

The carbon is preferably in particulate form e.g. as pellets. The size of the carbon particles will depend on the pressure drop acceptable in any given reactor (which gives a minimum pellet size) and reactant diffusion constraint within the pellet (which gives a maximum pellet size). The preferred minimum pellet size is 0.5 mm and the preferred maximum is 5 mm.

The carbons are preferably porous carbons. With the preferred particle sizes the carbons will need to be porous to meet the required surface area characteristics.

Carbons may be characterised by their BET, basal plane, and edge surface areas. The BET surface area is the surface area determined by nitrogen adsorption using the method of Brunauer Emmett and Teller Am Chem. Soc. 60,309 (1938). The basal plane surface area is the surface area determined from the heat of adsorption on the carbon of n-dotriacontane from n-heptane by the method described in Proc.Roy.Soc. A314 pages 473–498, with particular reference to page 489. The edge surface area is the surface area determined from the heat of adsorption on the carbon of n-butanol from n-heptane as disclosed in the Proc.Roy.Soc. article mentioned above with particular reference to page 495.

The carbons for use in the present invention have a BET surface area of at least 100 $m^2/g$, preferably at least 200 $m^2/g$, most preferable at least 300 $m^2/g$. The BET surface area is preferably not greater than 1000 $m^2/g$, more preferably not greater than 750 $m^2/g$.

The ratio of BET to basal plane surface area is not greater than 4:1 preferably not greater than 2.5:1, most preferably not greater than 2:1. It is particularly preferred to use carbons with ratios of BET to basal plane surface area of not greater than 1.5:1.

It is preferred to use carbons with ratios of basal plane surface area to edge surface area of at least 10:1, preferably at least 100:1, but preferably not more than 200:1.

The preferred carbon support may be prepared by heat treating a carbon-containing starting material. The starting material may be an oleophilic graphite e.g. prepared as disclosed in GB Pat. No. 1 168 785 or may be a carbon black.

However oleophilic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal. The materials subjected to the heat treatment preferably have particle sizes not less than these indicated above as being preferred for the carbon support.

The preferred starting materials have the following characteristics: BET surface area of at least 100, more preferably at least 500 $m^2/g$.

The preferred heat treatment procedure for preparing carbon supports having the defined characteristics, comprise successively: (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° and 600° C., and the heating in inert gas is preferably carried out at temperatures above 1500° C.

The duration of the heating in inert gas is not critical. The time needed to heat the carbon to the required maximum temperature is sufficient to produce the required changes in the carbon.

The oxidation step must clearly not be carried out under conditions such that the carbon combusts completely. It is preferably carried out using a gaseous oxidizing agent fed at a controlled rate to avoid over oxidation. Examples of gaseous oxidizing agents are steam, carbon dioxide, and gases containing molecular oxygen e.g. air. The oxidation is preferably carried out to give a carbon weight loss of at least 10% wt based on weight of carbon subjected to the oxidation step, more preferably at least 15% wt.

The weight loss is preferably not greater than 40% wt of the carbon subjected to the oxidation step, more preferably not greater than 25% wt of the carbon.

The rate of supply of oxidizing agent is preferably such that the desired weight loss takes place over at least 2 hours, more preferably at least 4 hours.

Where an inert atmosphere is required it may be supplied by nitrogen or an inert (Group 0) gas, e.g. argon, helium.

The total quantities of Group VIII metal/metal present in the catalyst are preferably in the range 0.1 to 50%, more preferably 1 to 30%, most preferably 5 to 10% of the total weight of catalyst.

The total weight of Group I, Group II metal, lanthanide and actinide is preferably in the range 0.1 to 4 times the weight of Group VIII metal, more preferably 1 to 2 times the weight of Group VIII metal.

The hydrogenation reaction is preferably carried out in the temperature in the range 150° to 400° C., more preferably 180° to 350° C. The pressure is preferably from 1 to 100 kPa, more preferably 1 to 20 kPa. The pressure must of course not be so high that the ester is in the liquid phase at the reaction temperature used.

The molar ratio of hydrogen to ester may for example be in the range 2:1 to 100:1, preferably 4:1 to 6:1. The total gas hourly space velocity over the catalyst may for example be in the range of 100 to 120,000, preferably 100 to 12000.

The invention will now be described by reference to the following examples.

EXAMPLE 1

The carbon used as support was prepared from a commercially available activated carbon sold by Degussa under the designation BK IV. The activated carbon was heat treated as follows. The carbon was heated from room temperature in a stream of argon to 1700° C. over a period of about one hour. When the temperature reached 1700° C. the carbon was allowed to cool in the stream of argon to 25° C. The carbon was the heated in air in a muffle furnace at approximately 520° C. for a time known from experience to give a weight loss of 20% wt. The carbon was then heated in argon to between 1800° C. and 1850° C. in argon. The carbon was allowed to cool to room temperature in an argon atmosphere. The resulting graphite-containing carbon was then ground to 16–30 mesh BSS.

This graphite-containing carbon had the following characteristics:
BET surface area: 550 $m^2/g$
basal plane area: 393 $m^2/g$
edge surface area: 1.2 $m^2/g$
giving BET/basal plane area: 1.4
basal plane/edge surface area of: 328

The carbon was impregnated with a 10% wt aqueous solution of ruthenium trichloride. Water was evaporated from the carbon in a rotary evaporator and the carbon was then dried in an oven at 100° C. It was then reduced in a stream of hydrogen at 450° C. for 2 hours. Potassium was then added by impregnating with a 20% wt solution of potassium nitrate, and evaporating and drying as before.

The resulting catalyst comprising ruthenium (8.9% weight of ruthenium based on total weight of catalyst) in the form of the metal and potassium (13.3% weight of potassium based on the weight of total catalyst) as the nitrate is charged to a micro-reactor in the form of a tube provided with means for passing a stream of hydrogen gas over the catalyst. The quantity of catalyst used was 0.1 g. The catalyst was reduced in situ in hydrogen at 300° C. until no more water was given off. The hydrogen flow is then diverted through a constant temperature reservoir of dried ethylacetate to produce a feed containing hydrogen and ethylacetate in the approximate molar ratio of 6:1 with a weight hourly space velocity (WHSV) = weight feed per hour/wt of catalyst of 8 $hr^{-1}$.

This feed was brought into contact with the catalyst at 300° C. and 7% conversion to products occurred. The selectivity to ethanol was 37%. The other products were mainly methane and water.

EXAMPLE 2

A carbon support was prepared using substantially the same technique as in Example 1.

The resulting carbon had the following properties.
BET surface area: 710 $m^2/g$
basal plane surface area: 389 $m^2/g$
edge surface area: 2.3 $m^2/g$
BET/basal surface area ratio: 1.83
basal plane/edge surface area ratio: 169

An experiment was carried out as in Example 1 except that the catalyst was prepared using nickel nitrate dissolved in 50% water/50% methanol (volume) and the nickel nitrate was reduced at 400° C. in hydrogen contained 5.1 wt % of nickel based on the total weight of catalyst.

The conversion of the ethyl acetate was 5% and the selectivity to ethanol was about 30%.

Those skilled in hydrogenation will readily understand that although the conversion is low, unreacted ester can be recycled and that therefore it is important to achieve a high selectivity.

COMPARATIVE TEST A

An experiment was carried out as in example 1 but in which no potassium was introduced into the catalyst. The resulting catalyst contained 8.2% by weight of ruthenium (based on weight of total catalyst). The conversion was 33% but the products were mainly acetic acid, methane and water. Little or no ethanol was produced.

COMPARATIVE TEST B

An experiment was carried out as in Example 2 but using palladium instead of nickel.

The conversion obtained was 9% and the selectivity to ethanol was less than 1%. Acetic acid was the only product. Experiments were carried out with Ru containing catalysts similar to the catalyst used in Example 1 but using lanthanum and calcium in place of potassium. Ethanol was produced with selectivities of 34% and 36%.

I claim:

1. A process for the production of an alcohol by hydrogenation of an ester of a carboxylic acid having 1 to 20 carbon atoms with a hydrogenation catalyst comprising a Group VIII element, a promoter, and a carbon support is characterised in that (1) the Group VIII element is ruthenium, nickel, or rhodium, (2) the promoter is introduced on to the carbon as a water stable compound of Group IA, metal excluding lithium Group IIA metal excluding beryllium and magnesium, a lanthanide or actinide, and (3) the carbon has a BET surface area of at least 100 $m^2/g$, and a ratio of BET to basal plane surface area not greater than 4:1, and (4) the hydrogenation is carried out in the vapour phase at a temperature in the range 100° C. to 400° C. at a total gas hourly space velocity of 100 to 120 000.

2. A process according to claim 1 wherein the hydrogenation reaction is carried out at a temperature in the range 180° to 350° C.

3. A process according to either of claim 2 wherein the pressure is in the range 1 to 100 kPa.

4. A process according to claim 2 wherein the molar ratio of hydrogen to ester is in the range 2:1 to 100:1.

5. A process according to claim 1 wherein the total gas hourly space velocity over the catalyst is in the range 100 to 1200.

6. A process according to claim 1 wherein the ester is an ester of a carboxylic acid having from 1 to 20 carbon atoms in the molecule and a primary alcohol.

7. A process according to claim 1 wherein the carbon has a BET/basal plane surface area ratio of 2.5:1.

8. A process according to claim 1 wherein the ratio of basal plane surface area to edge surface area is at least 10:1.

9. A process according to claim 8 wherein the ratio of basal plane surface area to edge surface area is at least 100:1.

* * * * *